(12) United States Patent
Johnson et al.

(10) Patent No.: US 8,303,620 B2
(45) Date of Patent: *Nov. 6, 2012

(54) TORNIQUET ARTICLE

(75) Inventors: Jennifer L. Johnson, Anderson, SC (US); Ross Johnson, Anderson, SC (US)

(73) Assignee: Tactical Medical Solutions, Inc., Anderson, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/841,475

(22) Filed: Jul. 22, 2010

(65) Prior Publication Data

US 2011/0178546 A1  Jul. 21, 2011

Related U.S. Application Data

(63) Continuation of application No. 10/830,144, filed on Apr. 21, 2004, now Pat. No. 7,776,064.

(51) Int. Cl.
*A61B 17/00* (2006.01)

(52) U.S. Cl. ............................................ 606/203; 602/5

(58) Field of Classification Search .......... 606/201–204; 602/5, 19

See application file for complete search history.

(56) References Cited

U.S. PATENT DOCUMENTS

| | | | |
|---|---|---|---|
| 2,387,428 A * | 10/1945 | Brothers | 606/203 |
| 6,899,720 B1 * | 5/2005 | McMillan | 606/203 |
| 7,776,064 B2 * | 8/2010 | Jennifer et al. | 606/203 |
| 2003/0028215 A1 * | 2/2003 | Brooks | 606/203 |

* cited by examiner

*Primary Examiner* — Victor Nguyen
(74) *Attorney, Agent, or Firm* — Cahn & Samules, LLP

(57) ABSTRACT

The present invention relates generally to first aid articles and more specifically tourniquets. One embodiment of the claimed subject matter includes a tourniquet article having a substantially rigid base. A handle is provided, the handle has first and second ends and a slot disposed between the first and second ends. A strap disposed adjacent to the substantially rigid base and passes through the slot of the handle. A structural member having first and second sides is attached to the base at least at first and second points along each of the first and second sides of the base such that the strap being sandwiched between at least a portion of the structural member and said base.

13 Claims, 2 Drawing Sheets

TORNIQUET ARTICLE

CROSS-REFERENCES TO OTHER RELATED PATENT APPLICATIONS

This application is a continuation of application Ser. No. 10/830,144 filed Apr. 21, 2004, now allowed, which is incorporated herein by reference.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISK APPENDIX

Not Applicable.

BACKGROUND OF THE INVENTION

1. Field of the Invention

The present invention relates to medical devices used in first aid. More specifically, this invention relates to improvements in tourniquets used for emergency medical use.

2. Description of Related Art

Tourniquet cuffs are used primarily to achieve occlusion of arterial bloodflow. A typical tourniquet is a tightly tied band applied around a body part (an arm or a leg) in an attempt to stop severe bleeding or uncontrolled hemorrhage in an emergency situation. Tourniquets frequently found in the prior art consist of tightly tied bands that are applied around a body part such as an arm or a leg to stem the flow of blood. In one example of the application of a tourniquet, a piece of rubber tubing is wrapped around the limb and tied tightly. A stick is wound underneath the tubing and twisted until the tubing is tightened so that the bleeding is stopped. The tubing must not be tightened more than what is required to stop the bleeding. Once an adequate pressure on the limb is achieved, the stick is tied into its position with additional tubing or bandages. Other items that can be used for a tourniquet include a belt, rope, string, wire, twine, and sections of clothing.

BRIEF SUMMARY OF THE INVENTION

The present invention relates generally to first aid articles and more specifically tourniquets. One embodiment of the claimed subject matter includes a tourniquet article having a substantially rigid base, a handle having first and second ends and having a slot disposed between the first and second ends; a strap disposed adjacent to the substantially rigid base and passing through the slot of the handle; and a structural member having first and second sides, the structural member being fixedly attached to the base at least at first and second points along each of the first and second sides, the strap being sandwiched between at least a portion of the structural member and said base.

In another embodiment, a locking ring is attached to the structural member.

In further embodiment of the invention, at least one of the first and second ends of the handle is configured to engage with the locking ring.

In yet another embodiment of the invention, the locking ring is operatively associated with the handle and at least one of the first and second ends of the handle includes a latching section that engages the locking ring.

In still another embodiment of the invention, tourniquet article includes a handle having first and second ends and having a slot disposed between the first and second ends; a substantially rigid base underlying the handle; a strap configured to be tightened about an injured limb by twisting the handle, the strap being engaged with the handled and being engaged with the substantially rigid base at i) a first point upstream from said handle and ii) at a second point downstream from the handle such that said substantially rigid base is maintained in underlying relationship to the handle thereby reducing binding of the substantially rigid base when the handle is twisted; and a means for locking said handle in place.

Having thus described embodiments of the present invention, it is the principal object of the present invention to provide an improved tourniquet article that can be used on a limb using one hand to place and secure the tourniquet article.

BRIEF DESCRIPTION OF THE SEVERAL VIEWS OF THE DRAWINGS

The above and other objects, advantages and features of the present invention will be more readily apparent from the following description, when read in conjunction with the accompanying drawings wherein.

DETAILED DESCRIPTION OF THE INVENTION

The present invention makes use of lightweight and rugged materials which allows the article to be carried into the field. This invention also allows the user to apply the tourniquet article with one hand instead of two which can be a crucial lifesaving feature in the battlefield when assistance from a medic is not immediately available and the injured still has some ability to prevent a large loss of blood in his or her body. The tourniquet can also be used in emergency first aid for animals such as horses.

Figure 1:
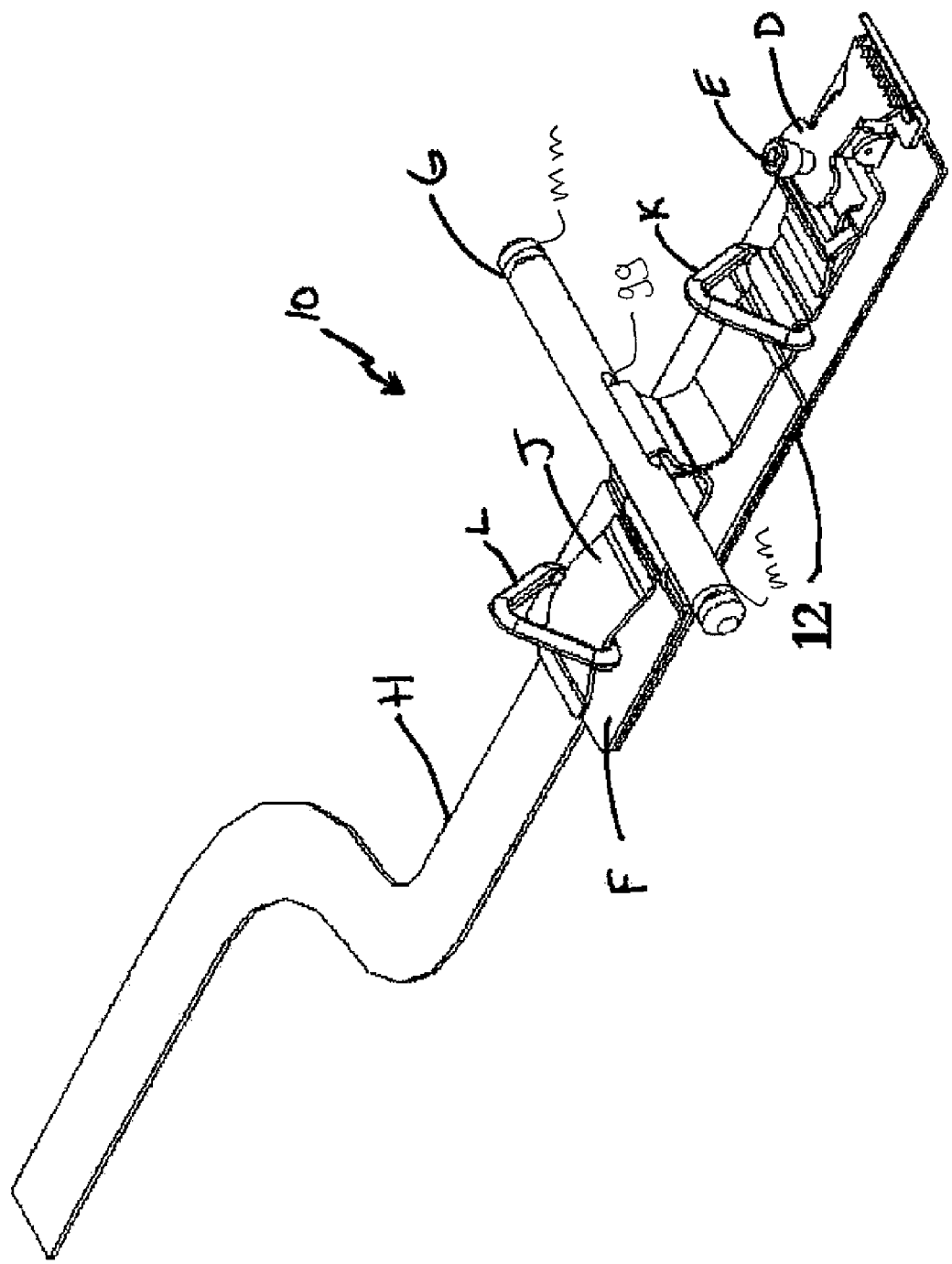
FIG. 1 is a perspective view of an embodiment of the claimed subject matter.
Figure 2:
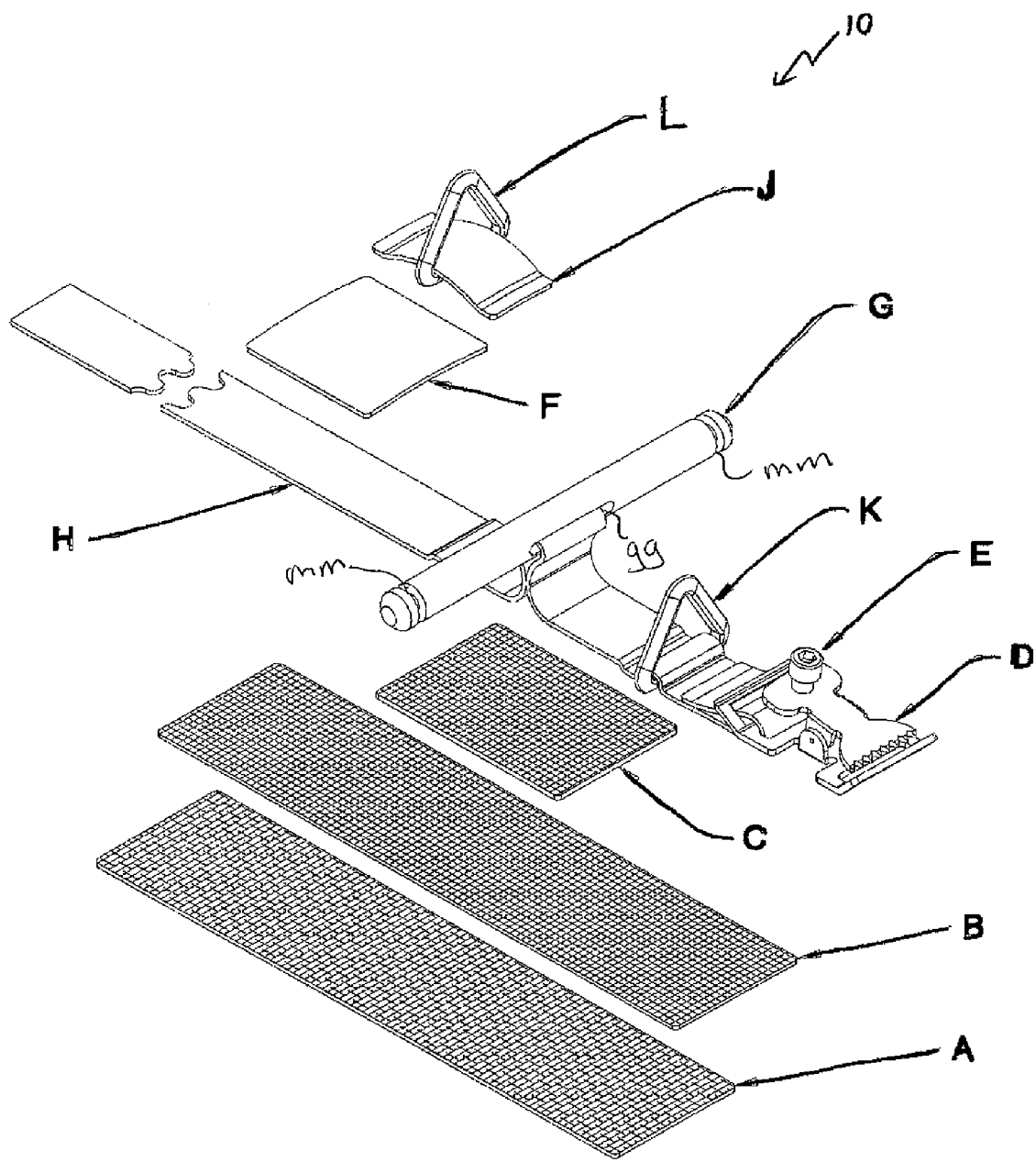
FIG. 2 is a diagram illustrating the components of an embodiment of the claimed subject matter.

Turning now descriptively to the drawings, in which similar reference characters denote similar elements throughout the views, FIGS. 1 and 2 illustrate an embodiment of the tourniquet article designated generally by the numeral 10.

The tourniquet article 10 as shown in FIGS. 1 and 2 comprises an elongated assembly of multiple components. Illustrated in FIG. 2 is a component view of the article 10. Base 12 is made of a 2"×8'/2" section of webbing B, a 2"×8'/2" section A of looped end Velcro® affixed to the under side of the webbing B, and a 2"×3" piece of webbing C affixed to the upper side of the webbing B. Webbing B is made of a 16 point heavy weight polypropylene material and webbing C is made of nylon scuba webbing but each can be made of any other suitable material, for example webbing C can be made of a plastic material. Section A can also be made of a non skid or non slip fabric or any other suitable material.

The separate sections can be joined or combined by sewing, bonding or by using any suitable means. In the present embodiment, webbing B and section A are sewn together. The looped end of Velcro® Section A is positioned so the bottom-most layer of loop is in contact with the limb when the tourniquet article 10 is used. Section A is used in this embodiment to increase friction between the tourniquet article 10 and the limb and to provide padding between webbing B and the tissue of the limb. Section A also helps protect the skin and soft tissue from pinching and bruising that can be associated with the use of the tourniquet article 10. Section A also helps the user in applying tourniquet article 10 by holding the tourniquet in place and allowing the user to apply article 10 with one hand.

Webbing C is attached to the upper facing side of webbing B about 2" in distance from the end of the webbing B base positioned beneath the handle G. Scuba nylon webbing is used for webbing C in the present embodiment to increase the rigidity of the base 12 and to prevent binding or crushing of base 12 when handle G is twisted or turned. In another embodiment, several sections of scuba webbing can also be used together as webbing C instead on one section, and this can further facilitate the needs of rigidity while still being flexible enough for use with a limb in addition to making article 10 easier to store and carry. Velcro® section A, webbing B and webbing C can each be constructed of scuba webbing and additionally, each section of base 12 can be lengthened, shortened, narrowed or widened. Additional padding can also be added to base 12, or individually to section A, webbing B or webbing C. One or more adhesive strips may also be used to bond one or more of these sections of base 12.

In this embodiment, cap F is positioned and attached to the top of base 12. Cap F maintains the strap H in proximity to the base 12 and as such maintains strap H in flat orientation in relation to base 12. Cap F is a 2 inch by 2 inch section of nylon scuba webbing sewn on to base 12 along the two edges or outer sides of webbing B. Cap F can also be made of a plastic sleeve, or a combination of plastic and polypropylene webbing which can be used to increase the rigidity of cap F. Cap F can also be bonded or attached in any suitable manner to base 12. Cap F functions helps maintain the form of strap H when strap H is being tightened and it also helps prevent twisting of the strap H before strap H is tightened around the top of base 12. Cap F maintains the form of strap H by working in conjunction with base 12 acting as a rigid sleeve or a sandwich in which strap H must pass through before making contact with the limb.

In this embodiment, cap F also provides a point of attachment for the second locking ring without interfering with the function of strap H. Base 12 and cap F can also be made thinner and with lighter weight material so that the tourniquet article is more pliable and less bulky depending on the needs of the user. This reduction of bulk can make it easier in some situations to apply the tourniquet article 10 to a limb, but in all the embodiments, base 12 and cap F maintain a flat surface against the limb to help prevent cuff migration.

The tightening system consists of handle G, strap H, and buckle D. Handle G is constructed of ½" TO16 aircraft grade aluminum rods cut to a length of 5.5 inches Handle G includes bevels and notches mm on the surface area at each end of handle G to facilitate the securing of handle G into the locking rings. Handle G also has a 0.156"×1.219" aperture/slot gg positioned in the center of handle G which allows for the passage of strap H. The slot gg is slightly wider than strap H which allows more leeway in movement of handle G during tightening of tourniquet article 10 as well as making the article easier to fold and compact for storage. Handle G can also be gnarled, notched or beveled on one or more sides to provide a tighter grip to the user for purpose of tightening the tourniquet article 10. Handle G can also be longer or shorter, made of a larger or smaller diameter, or made of another suitable material such as nylon, plastic, or composite.

Buckle D is a quick release type buckle which allows the user to quickly release strap H. The quick release buckle used in the present embodiment is a standard one inch buckle tapped to accept a ¼ inch machine screw. Buckle D can be any other suitable buckle such as a Fastek 1 and ½ inch buckle and it can also be a different size and dimension. The machine screw threads into the top of the buckle and the head rests on the base of the buckle. When engaged, Buckle D prevents accidental loosening of the tourniquet should buckle D be accidentally bumped or moved while the patient is being transported. Further, cap screw B can be used to help prevent movement of the strap H. In this embodiment, optional cap screw B is positioned in the top of cap F so as to allow the user to tighten the screw down the strap H further securing the strap H against unintended loosening. Cap screw E is a 'A"× ⅝" socket head cap screw, but it can be any desired width and length.

Strap H is made of 16 point heavy weight polypropylene webbing that is 1 inch in width and 46 inches in length. It can also be made of any suitable size or material. For example, it can range from 1 inch in width to 2 and ½ inches in width. It can also be longer or shorter than 46 inches in length, and the material it is made of can be nylon webbing instead of polypropylene. One end of strap H is routed around the quick release buckle and attached to base 12. In the present embodiment, Strap H is sewn to base 12. The free end of Strap H is first routed through ring K and attached to base 12. From the point of attachment to base 12, the free end of Strap H is then routed through the aperture in handle G and sewn back onto itself forming a small loop that holds the handle in position with strap H. This loop is designed to provide enough slack so that twisting handle G does not cause base 12 to bind or twist. Once strap H is positioned to hold handle G, it is routed through the area above base 12 and below cap F so that the other end remains free to use by the user to be placed into the quick release buckle D in order to tighten the tourniquet article 10. Strap H can also be secured directly to base 12 with an allowance for a loop to run through handle G.

As shown in FIGS. 1 and 2, rings K and L are used to in the present embodiment to secure strap H to base 12, but only one ring needs to be used. The rings are used to secure strap H in place when tourniquet article 10 is in use. Rings K and L consist of two 1" actyl tri-rings. The rings can be of any suitable type such as D type or 0 type rings, they can also be made to swivel, and they can be made of any suitable material such as steel or aluminum.

Ring K is secured to base 12 adjacent to the quick release buckle D. Strap H runs from the quick release buckle D to ring K where strap H is sewn to the base 12. Ring K is then positioned on the upper surface of strap H and, using a section of webbing which is placed over ring K and sewn to base 12, ring K is secured to strap H. Ring K is not able to freely move along the length of strap H, but ring K can be folded over to aid in storage. Ring L is positioned on the upper surface of cap F. Ring L is secured to cap F with a 1 inch by 2 inch 16 point polypropylene webbing J with the sides of webbing J sewn to cap F covering the lower portion of ring K. In this fashion, ring L can be moved closer or farther away from handle G so ring L can be positioned to assist locking handle G in place after tension has been applied to tourniquet article 10. In other embodiments, the one or more rings can be positioned on base 12 or cap F and any on of them can be attached directly or any one can have the ability to slide.

Tourniquet article 10 is used in this embodiment with two rings which allow article 10 to be adjusted to fit different sized and shaped limbs, for example limbs having conical or non-cylindrical shapes, and which allow either or both ends of handle G to be inserted into one or both rings K and L to secure the handle G against slippage. In other instances, it may be desired to use more than two rings to allow more binding points at which strap H can be routed through allowing an even tighter fit for most uses. Base 12 can also be widened to give a greater tissue area allowing less pressure to be used to achieve hemostasis.

Initially, tourniquet article 10 should be broken in by applying article 10 to a solid object and tightening the handle two to three times to loosen the webbing. This breaking in facilitates later one handed use. Article 10 is stored in a bag or pouch with strap H running through buckle D and safety cap screw E slightly loosened. To deploy tourniquet article 10 in a situation where one limb is disabled, strap H is grasped with the uninjured arm and tourniquet article 10 is slid over the injured extremity. Strap H is pulled as quickly as possible to remove excess slack in strap H and to initially tighten article 10 around the injured limb. Handle G is twisted until the bleeding is controlled and then handle G is latched into one or both rings K and L. It is not necessary to latch both ends of the handle G. The cap screw E located on quick release buckle D is then tightened to help prevent accidental loosening, and further medical treatment is sought.

While the present invention has been illustrated and described by means of specific embodiments and alternatives, it is to be understood that numerous changes and modifications can be made without departing from the spirit and scope of the invention. Therefore, it should be understood that the invention is not to be limited in any way except in accordance with the appended claims and their equivalents.

What is claimed is:

1. A tourniquet article comprising:
   a substantially rigid base;
   a substantially cylindrical handle having first and second ends and having a slot disposed between the first and second ends;
   a strap disposed adjacent to said substantially rigid base and passing through the slot of said handle, said substantially cylindrical handle being rotatably coupled with said substantially rigid base;
   a structural member having first and second sides, said structural member being fixedly attached to said substantially rigid base at least at first and second points along each of the first and second sides, said strap being sandwiched between at least a portion of said structural member and said base; and
   means for blocking rotation of said substantially cylindrical handle.

2. The tourniquet article of claim 1 further comprising a locking ring attached to said structural member.

3. The tourniquet article of claim 2 wherein at least one of the first and second ends of said handle includes a latching section configured to engage with said locking ring.

4. The tourniquet article of claim 1 further comprising a locking ring operatively associated with said handle and wherein at least one of the first and second ends of said handle includes a latching section that engages said locking ring.

5. The tourniquet article of claim 1 wherein said substantially rigid base includes a hook and loop fastener.

6. The tourniquet article of claim 1 wherein said substantially rigid base includes a non-slip fabric.

7. The tourniquet article of claim 1 wherein said substantially rigid base includes means for preventing binding of said substantially rigid base when said handle is turned.

8. A tourniquet article comprising:
   a handle having first and second ends and having a slot disposed in a center of said handle, said handle being rotatable with respect to a substantially rigid base;
   the substantially rigid base underlying said handle;
   a strap configured to be tightened about an injured limb by twisting said handle, said strap being engaged with said handled and being engaged with said substantially rigid base at i) a first point upstream from said handle and ii) at a second point downstream from said handle such that said substantially rigid base is maintained in underlying relationship to said handle thereby reducing binding of said substantially rigid base when said handle is twisted; and
   means for locking said handle in place.

9. The tourniquet article of claim 8 wherein said substantially rigid base includes a hook and loop fastener.

10. The tourniquet article of claim 8 wherein said substantially rigid base includes a non-slip fabric.

11. The tourniquet article of claim 8 wherein said substantially rigid base includes means for preventing binding of said substantially rigid base when said handle is turned.

12. The tourniquet article of claim 8 further comprising means for maintaining said strap in substantially flat orientation in relation to said substantially rigid base.

13. The tourniquet article of claim 8 wherein said handle is substantially cylindrical.

* * * * *